United States Patent
Hefny et al.

(10) Patent No.: US 9,562,885 B2
(45) Date of Patent: Feb. 7, 2017

(54) IONOPHORE AND POLYMER MEMBRANE SELECTIVE FOR ALUMINUM (III) ION

(71) Applicant: UMM AL-QURA UNIVERSITY, Makkah (SA)

(72) Inventors: Amr Lotfy Saber Hefny, Makkah (SA); Abd El-Shafey Ahmed, Zagazig (EG)

(73) Assignee: Umm Al-Qura University, Makkah (SA)

( * ) Notice: Subject to any disclaimer, the term of this patent is extended or adjusted under 35 U.S.C. 154(b) by 131 days.

(21) Appl. No.: 13/897,310

(22) Filed: May 17, 2013

(65) Prior Publication Data

US 2014/0339079 A1 Nov. 20, 2014

(51) Int. Cl.
*G01N 27/40* (2006.01)
*G01N 33/18* (2006.01)
*G01N 27/333* (2006.01)

(52) U.S. Cl.
CPC ...... *G01N 33/1813* (2013.01); *G01N 27/3335* (2013.01)

(58) Field of Classification Search
CPC ............. G01N 27/3335; G01N 33/1813
See application file for complete search history.

(56) References Cited

U.S. PATENT DOCUMENTS 2,874,146 A * 2/1959 Raymond et al. ............ 524/169
5,102,527 A * 4/1992 Shibata et al. ............... 204/416
5,236,570 A 8/1993 Ma et al.
5,415,746 A 5/1995 Cha
(Continued)

FOREIGN PATENT DOCUMENTS

CA 2117692 A1 11/2004
EP 0490631 A2 6/1992
(Continued)

OTHER PUBLICATIONS

Buhlmann et al., "Carrier-Based Ion-Selective Electrodes and Bulk Optodes. 2. Ionophores for Potentiometric and Optical Sensors", Chem. Rev. 1998, 98, 1593-1687.
(Continued)

*Primary Examiner* — Michael B Nelson
(74) *Attorney, Agent, or Firm* — Richard C. Litman

(57) ABSTRACT

The ionophore and polymer membrane selective for aluminum (III) ion provide an ionophore that is selective for aluminum (III) ion [$Al^{3+}$].

The ionophore may be used as a dopant in a polymer membrane formed from a polymer matrix, e.g., poly (vinyl chloride) (PVC), and that may also include a plasticizer, such as dioctylphthalate (DOP) and o-nitrophenylloctyl ether (o-NPOE). The polymer membrane may be incorporated into an ion selective electrode (ISE) that can be used as a potentiometric sensor for the detection of $Al^{3+}$ ions in wastewater. The ionophore is diethyl (2-azobenzoic acid) malonate, which has the structure:

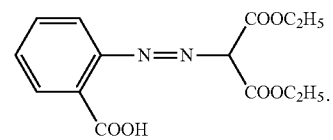

6 Claims, 1 Drawing Sheet

(56) References Cited

U.S. PATENT DOCUMENTS 5,417,835 A    5/1995   Brown et al.
5,607,567 A    3/1997   Yun et al.

FOREIGN PATENT DOCUMENTS

EP            767372 A1    4/1997
WO    WO 2005/008232 A1    1/2005

OTHER PUBLICATIONS

Saleh et al., "Novel potentiometric membrane sensor for selective determination of aluminum(III) ions", *Analytica Chimica Acta*, vol. 434, Issue 2, May 11, 2001, pp. 247-253.
Abbaspour et al., "Aluminium(III)-selective electrode based on a newly synthesized tetradentate Schiff base", *Talanta*, vol. 58, Issue 2, Aug. 23, 2002, pp. 397-403.

* cited by examiner

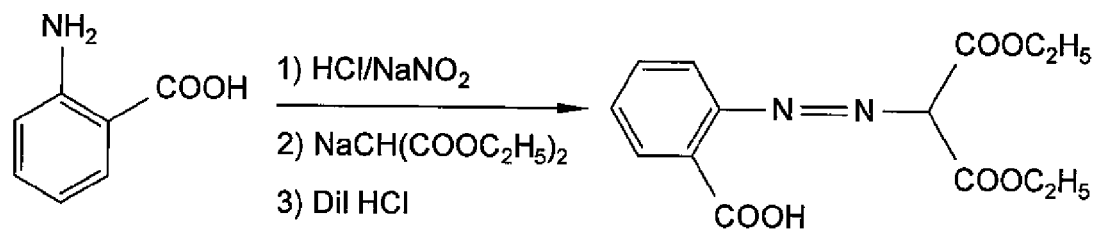

IONOPHORE AND POLYMER MEMBRANE SELECTIVE FOR ALUMINUM (III) ION

BACKGROUND OF THE INVENTION

1. Field of the Invention

The present invention relates to electrode sensors, and particularly to an ionophore and a polymer membrane selective for aluminum (III) ion.

2. Description of the Related Art

Potentiometric sensors typically use an ion selective electrode (ISE). The voltage between a reference electrode and the ISE exposed to an analyte solution can be measured, and since this voltage is related to the activity of the analyte by the Nernst equation, the unknown concentration of the analyte can be computed. There are several different types and configurations of ion selective electrodes, with and without internal reference solutions. The ISE usually uses a semipermeable membrane or selectively permeable membrane that is selective for the cation or anion of interest. One type of membrane used in an ion selective electrode is a polymer membrane. The polymer membrane includes a polymer matrix, often of poly (vinyl chloride) (PVC), that is doped with an ionophore (an organic ion exchange agent). The membrane also may include a plasticizer to keep the polymer soft and amorphous so that the ion of interest can be transported between the aqueous analyte solution and the ionophore embedded in the polymer matrix. The plasticizer may also affect the dielectric constant of the polymer membrane. Plasticized polymers used for ISE membranes are sometimes described as viscous liquids and referred to in the literature as liquid membranes.

Wastewater often contains aluminum ions ($Al^{3+}$). However, conventional aluminum sensors for detecting and measuring such contamination suffer from a wide variety of limitations, such as cost and difficulty in use. Thus, an ionophore and polymer membrane selective for aluminum (III) ion solving the aforementioned problems is desired.

SUMMARY OF THE INVENTION

The ionophore and polymer membrane selective for aluminum (III) ion provide a novel ionophore that is selective for aluminum (III) ion [$Al^{3+}$]. The ionophore is diethyl (2-azobenzoic acid) malonate, having the formula:

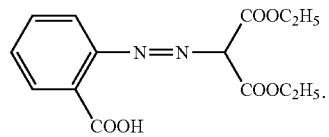

The ionophore may be used as a dopant in a polymer membrane formed from a polymer matrix, e.g., poly (vinyl chloride) (PVC), and that may also include a plasticizer, such as dioctylphthalate (DOP) and o-nitrophenyloctyl ether (o-NPOE). The polymer membrane may be incorporated into an ion selective electrode (ISE) that can be used as a potentiometric sensor for the detection of $Al^{3+}$ ions in wastewater.

These and other features of the present invention will become readily apparent upon further review of the following specification.

BRIEF DESCRIPTION OF THE DRAWINGS

The sole FIGURE is a reaction scheme for the synthesis of the ionophore selective for aluminum (III) ion according to the present invention.

Similar reference characters denote corresponding features consistently throughout the attached drawing.

DETAILED DESCRIPTION OF THE PREFERRED EMBODIMENTS

The ionophore and polymer membrane selective for aluminum (III) ion provide a novel ionophore that is selective for aluminum (III) ion [$Al^{3+}$]. The ionophore is diethyl (2-azobenzoic acid) malonate and has the following structure:

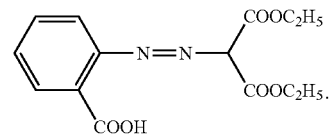

The ionophore may be used as a dopant in a polymer membrane formed from a polymer matrix, e.g., poly (vinyl chloride) (PVC), and that may also include a plasticizer, such as dioctylphthalate (DOP) and o-nitrophenyloctyl ether (o-NPOE). The polymer membrane may be incorporated into an ion selective electrode (ISE) that can be used as a potentiometric sensor for the detection of $Al^{3+}$ ions in wastewater.

The polymer may be any polymer conventionally used for making a polymer membrane for an ISE, and may be selected from the group consisting of poly (vinyl chloride), silicone rubbers, polyurethanes, acrylates, perfluoropolymers, and polyaniline. The ionophore is diethyl (2-axobenzoic acid) malonate. When the polymer matrix is a soft, amorphous polymer, such as some silicone rubbers, no plasticizer may be needed. However, when the polymer is a hard, brittle glass at room temperature, a plasticizer must be added. The plasticizer may be at least one plasticizer selected from the group consisting of dioctylphthalate (DOP), dibutyl phthalate (DBP), tricresil phthalate (TCP), dibutylsebacate (DBS), and o-nitrophenyloctyl ether (o-NPOE). In addition, the polymer membrane may contain an additive, such as sodium tetraphenylborate (NaTPB), that acts as an anion excluder and helps to lower the detection limit for cations.

Example 1

The following example describes one method for preparing the ionophore, although any method for preparing the ionophore may be used. The ionophore is made by first dissolving 3.5 g of anthranilic acid in hydrochloric acid (37%, 5 mL) and 15 mL of distilled water, and then cooling the solution to a temperature of about 4° C. At the same time, a sodium nitrite solution (1.75 g in 6 mL of distilled water) is prepared, cooled and then added drop-wise to the cooled solution of anthranilic acid dissolved in dilute hydrochloric acid. This addition results in a diazonium solution, which is then cooled in an ice bath for about 15 minutes.

To prepare the coupler, separately, 3.3 g of diethylmalonate is added to sodium ethoxide to form the coupler solution. The sodium ethoxide may be prepared by conventional methods, such as by dissolving 0.6 g of sodium metal in about 20 mL of absolute ethanol. The coupler solution is stirred for about 20 minutes at a temperature of about 60° C., and then cooled to a temperature of about 4° C. The cold diazonium solution is then added to the coupler solution drop-wise over a period of about one hour while maintaining the reaction temperature at about 4° C. to form a deep red, solid precipitate. The pH of the solution is adjusted to 7, and the precipitate is filtered out and washed thoroughly with cold water to obtain the ionophore, diethyl (2-azobenzoic acid) malonate. This synthesis is illustrated by the reaction scheme shown in the sole drawing FIGURE.

The precipitate was tested by infrared spectroscopy, $^1$H NMR, and elemental analysis, with the following results. FTIR (KBr): $v_{max}$ (CM$^{-1}$) 1708 (C=O, broad band), 2400-3400 (OH, carboxylic acid), 1390 (N=N), 3 peaks at 1596, 1570, and 1492 for the aromatic ring, 2984 (CH aliphatic), 3073 (CH aromatic) and 1103 (C—O). $^1$H NMR (DMSO-d6): δ 1.3 (t, 3H), 4.2 (q, 2H), 2.2 (s, 1H), 7.4 (m, 4H), 14.6 (s, 1H). Elemental analysis: found (%): C, 53.8; H, 4.8; N, 8.8. Calculated for $C_{14}H_{16}O_6N_2$ (%): C, 54.5; H, 5.2; N, 9.1.

Example 2

The polymer membrane was prepared as follows. The diethyl (2-azobenzoic acid) malonate ionophore (1.12-2.15%, w/w), prepared as described in Example 1, along with NaTPB (sodium tetraphenylborate) (0.28-1.08%, w/w), a plasticizer (53.63-73.28%, w/w, of DOP and o-NPOE), and poly (vinyl chloride) (24.42-36.64%, w/w), are then dissolved in about 6 ml of tetrahydrofuran (THF) to form a membrane solution. The diethyl (2-azobenzoic acid) malonate is provided in a weight percentage between about 1.12 wt % and about 2.15 wt % (w/w), the NaTPB is provided in a weight percentage between about 0.28 wt % and about 1.08 wt % (w/w), the plasticizer is provided in a weight percentage between about 53.63 wt % and about 73.28 wt % (w/w), and the poly (vinyl chloride) is provided in a weight percentage between about 24.42 wt % and about 36.64 wt % (w/w). The plasticizer is o-nitrophenyloctyl ether (o-NPOE) and dioctylphthalate (DOP).

The resulting solution is then poured onto a glass ring having an inner diameter of about 30 mm, which rests on a smooth glass plate. The THF is allowed to evaporate over about 48 hours at ambient temperature, leaving a transparent PVC matrix membrane having an average thickness of about 0.2 mm. The membrane is incorporated into an ISE and preferably conditioned by soaking in 0.01 mol/L aluminum solution for at least two days prior to use, and then is stored in the same solution.

The electrode revealed a Nernstian response over $Al^{3+}$ ion in a concentration range $1.0 \times 10^{-7}$ to $1.0 \times 10^{-1}$ mol/L with a detection limit of $2.8 \times 10^{-7}$ mol/L and a Nernstian slope of 19.6±0.1 mV/decade. The electrode showed good discrimination toward $Al^{3+}$ ion with respect to most common cations. It shows a short response time (10 s) for the entire concentration range and was used for two months without significant divergence in potentials. To evaluate the analytical applicability, the electrode was used to determine $Al^{3+}$ ion in different collected samples from environmental sources. In addition, the sensor has been used as an indicator electrode in potentiometric titration of $Al^{3+}$ ion against EDTA.

It is to be understood that the present invention is not limited to the embodiments described above, but encompasses any and all embodiments within the scope of the following claims.

We claim:

1. A polymer membrane selective for aluminum (III) ions, consisting of a membrane consisting of a polymer, dioctyl phthalate, o-nitrophenyloctyl ether, sodium tetraphenylborate, and an ionophore consisting of diethyl (2-azobenzoic acid) malonate.

2. The polymer membrane according to claim 1, wherein said polymer is selected from the group consisting of poly (vinyl chloride), silicone rubbers, polyurethanes, acrylates, perfluoropolymers, and polyaniline.

3. The polymer membrane according to claim 1, wherein said polymer comprises poly (vinyl chloride).

4. The polymer membrane according to claim 1, wherein said membrane consists of:
   between about 24.42 wt % and about 36.64 wt % (w/w) poly (vinyl chloride);
   between about 1.12 wt % and about 2.15 wt % (w/w) diethyl (2-azobenzoic acid) malonate;
   between about 53.63 wt % and about 73.28 wt % (w/w) dioctylphthalate and o-nitrophenyloctyl ether; and
   between about 0.28 wt % and about 1.08 wt % (w/w) sodium tetraphenylborate.

5. An ion selective electrode comprising the polymer membrane according to claim 4.

6. A method for determining an aluminum ion concentration in a sample comprising using the polymer membrane according to claim 1.

* * * * *